United States Patent [19]

Lewis

[11] 4,120,313
[45] Oct. 17, 1978

[54] COUPON HOLDER

[76] Inventor: Harvey L. Lewis, R.R. 4, Box 202, Independence, Kans. 67301

[21] Appl. No.: 773,744

[22] Filed: Mar. 2, 1977

[51] Int. Cl.² ............................................ G01N 33/00
[52] U.S. Cl. ..................................... 137/268; 422/53
[58] Field of Search ............. 137/268, 318; 23/230 C, 23/253 C; 73/86; 251/112, 116

[56] References Cited

U.S. PATENT DOCUMENTS

| 980,665 | 1/1911 | Ord | 73/421 B X |
|---|---|---|---|
| 1,689,236 | 10/1928 | Fraser | 251/112 X |
| 1,730,305 | 10/1929 | Stancu | 251/116 |
| 1,769,463 | 7/1930 | Rice | 73/86 |
| 2,770,532 | 11/1956 | Mason | 137/318 X |

Primary Examiner—Alan Cohan
Attorney, Agent, or Firm—Head, Johnson & Chafin

[57] ABSTRACT

An apparatus for inserting and removing a corrosion coupon from the interior of a pipeline while under pressure, comprises an elongated cylinder with a flange or threaded connection at one end and a closure device at the other end. The cylinder is attached to a valve which is attached as a branch to a pipeline. Inside of the cylinder are guides for the longitudinal movement of a long rack at the end of which is mounted the corrosion coupon. A pinion in operative relation to the rack is mounted on a shaft which is supported in a side pipe to the cylinder. A handwheel operating the shaft permits the longitudinal movement of a long rack within the cylinder. At the end of the rack is mounted the corrosion coupon. When the valve is open the coupon is moved through it into the pipeline so that the coupon is exposed to the fluid flowing in the pipeline. Indexing means is provided for determining the precise position of the coupon in the pipe.

3 Claims, 4 Drawing Figures

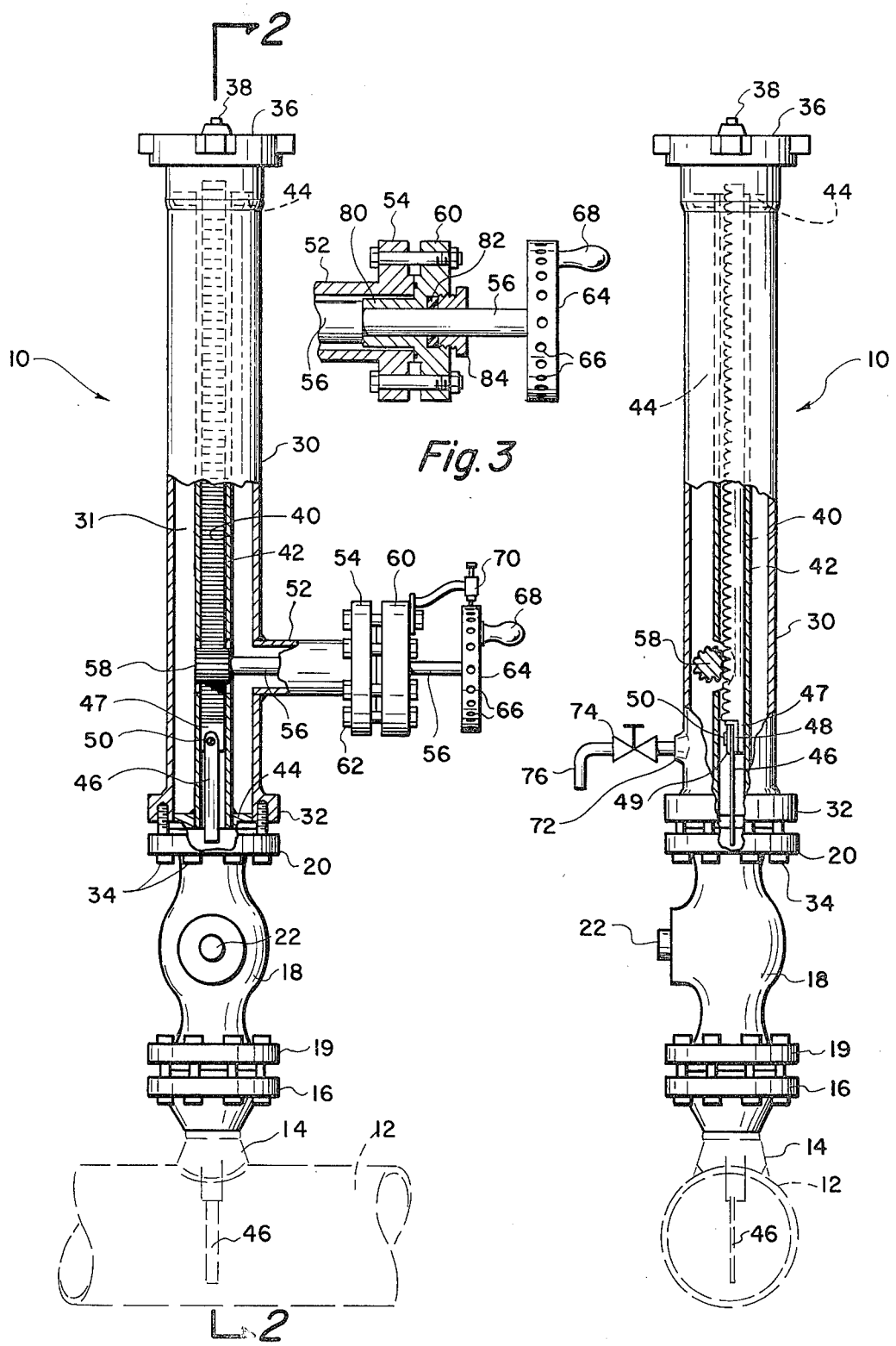

COUPON HOLDER

BACKGROUND OF THE INVENTION

This invention lies in the field of the measurement of the corrosive effect of fluid whether gases or liquids carried in pipelines. More particularly, this invention relates to an apparatus which can be attached to a pipeline and permits the introduction into and retrieval of a corrosion coupon from a pipeline, while the pipeline is under operating pressure.

It has been customary to determine the corrosiveness of a pipeline fluid so as to estimate the extent of corrosion to the interior surfaces of a pipeline, by inserting into the flowing fluid a coupon of metal of standardized size, shape, composition and finish. By visual inspection, or by measuring the loss of weight for a selected period of immersion in the fluid, the rate of corrosion can be determined. These coupons are generally inserted into the pipeline while the line is shut down, by removing a plug from the pipeline, inserting the coupon and then replacing the plug so as to seal the line against leakage.

A primary object of this invention is to provide an apparatus for inserting into and retrieving a corrosion coupon from the interior of a pipeline while the pipeline is operating and under fluid pressure.

It is a further object of this invention to provide a means of positioning a corrosion coupon inside a pipeline while the pipeline is under fluid pressure to precisely know the position of the coupon in the interior of the pipeline.

It is a still further object of this invention to support a corrosion coupon at a known position in the interior of a pipeline by means which electrically insulate the coupon from the pipeline structure, to minimize electrolyte corrosion.

SUMMARY OF THE INVENTION

These and other objects are realized and the limitations of the prior art are overcome in this invention by providing a branch to the pipeline with a valve attached to the branch. An elongated cylindrical casing is attached to the valve. Inside the elongated casing is a long rack supported in guides, so that it can be moved longitudinally by means of a pinion controlled by a handwheel and a shaft supported in a side arm to the elongated cylindrical casing. The coupon is attached to the end of the rack, so as the rack is traversed, the coupon is positioned inside the pipeline.

When the valve is closed, the pipeline can be under pressure, but the cylindrical casing or chamber can be reduced to atmospheric pressure by a pressure release valve. After the pressure is reduced, the end of the chamber opposite to that which is attached to the valve is removed. This is a rapid removal closure, which is a standardized piece of equipment, so that with a minimum of effort the end closure is removed. The rack is then longitudinally moved out of the chamber, and the coupon can be inspected or replaced. When the coupon is to be replaced inside the pipeline, it is mounted on the end of the rack and inserted into the open end of the cylinder and inside of the guides. The pinion then coacts with the rack and carries it to a position where it is completely inside the casing. The closure can then be applied and the chamber sealed. The valve is then opened allowing pipelines fluid pressure inside of the chamber, and providing a passage through the valve for the insertion of the coupon into the pipeline.

The handwheel that operates the pinion has an index and a locking means, so that in positioning the coupon, the handwheel is turned until the coupon reaches the opposite wall of the pipeline after which it is reversed in motion a selected distance. The handwheel is then locked by means provided.

BRIEF DESCRIPTION OF THE DRAWINGS

These and other objects and advantages of this invention and a better understanding of the principles and details of the invention will be evident from the following description taken in conjunction with the appended drawings in which:

FIG. 1 is an elevation view, in cross-section, of one embodiment of the apparatus of this invention.

FIG. 2 is a cross-sectional view taken along the line 5—5 of FIG. 1.

FIG. 3 shows a detail of the construction of one arrangement of the flange which supports the pinion shaft and handwheel.

DESCRIPTION OF THE PREFERRED EMBODIMENT

Figure 4:
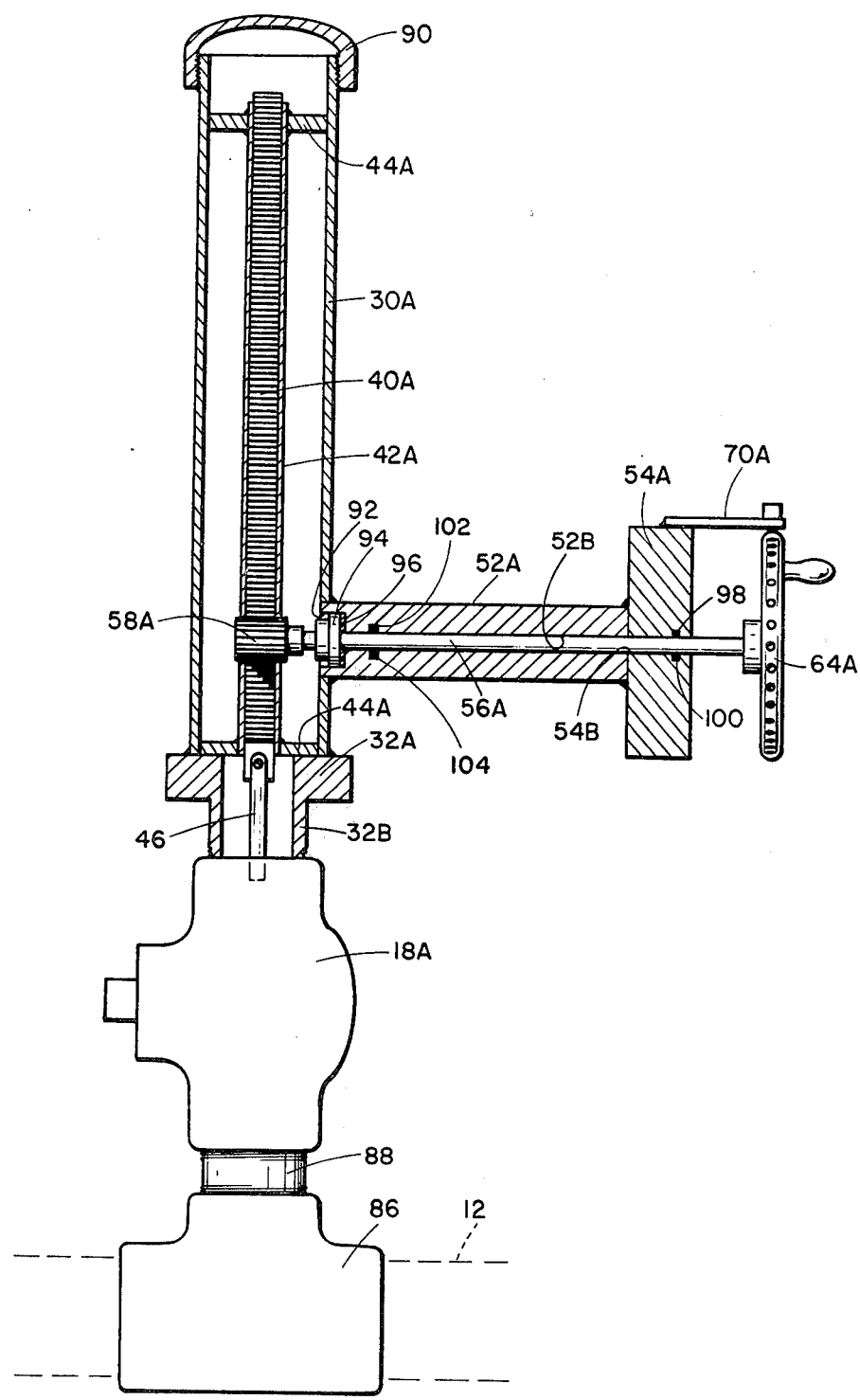
FIG. 4 is an elevational view in partial cross-section of an alternate embodiment of the invention emphasizing a more economical construction of the device.

Referring now to the drawings, the apparatus of this invention is indicated generally by the numeral 10. It comprises an elongated cylindrical pipe 30 which has a flange 32 on one end for attachment to the flange 20 of a valve 18 by means of bolts 34. The valve 18 is itself attached by flange 19 to a flange 16 attached as a side pipe 14 to the pipeline 12. The valve is of a type which has a clear passage, such as a ball valve, with operating shaft 22 so that by a 90° turn of the shaft 22 the valve can be changed from open to closed, thereby sealing the pressure in the pipeline from the space 31 inside of the chamber of the coupon holding apparatus.

The cylinder 30 has a quick opening and closing device 36 at its opposite end, so that by a small angle of rotation of the closure 36, it can be removed from the end of the cylinder 30.

There is a pressure release valve 38 of conventional design, which is part of the closure 36. The purpose of the relief valve 38 is to reduce the pressure to atmospheric, inside the space 31, in the cylinder 30, after the valve 18 has been closed, so that the closure 36 can be removed.

There is a long rack 40 which is guided longitudinally by guide 42 supported within cylinder 30. Guide 42 is in the form of a length of square cross-sectioned tubing. It is supported at each end to the interior of the cylinder 30 by means of brackets 44.

There is a side pipe 52 attached, as by welding, to the cylinder 30, which carries a flange 54. A matching flange 60 is designed to support a shaft 56 with a pressure seal such as shown in FIG. 3. The shaft 56 carries a pinion 58 which co-acts with the rack so that by rotation of the shaft 56 by means of the handwheel 64, and the handle 68, the rack can be traversed longitudinally inside of the chamber 30.

On the operating end of the rack is mounted a corrosion coupon 46 which is of standardized size, shape and material. It is attached to the end 47 of the rack 40 by means of a screw 50 and is insulated from the rack and screw by insulating washers 48 and 49. The insulating material is preferably teflon, which insulates the coupon from the metal of the rack, and the pipeline, so as to minimize corrosion by electrolytic processes.

In FIGS. 1 and 2, the pipeline 12, the side branch 14, flanges 16 and 19, and the valve 18 are shown in dashed lines, since they form no part of the invention, but are simply part of the pipeline to which the device of this invention, namely the coupon holder, are attached.

In operation, when the pipeline is under pressure and the valve 18 is closed, the coupon holder 10 can be attached by holding flange 32 of the chamber 30, to the flange 20 of the valve 18 by means of stud nuts and gaskets, as is conventionally done. The quick closure means 36 is attached and sealed. The valve 18 is then opened by rotating the shaft 22, providing an opening through the valve for the rack and coupon attached. The handwheel 64, which rotates the shaft 56 and pinion 58, traverses the rack longitudinally, so that the coupon passes through the valve 18 and into the pipe 12.

It is important to know the precise position of the coupon inside of the pipe. This is done by traversing the rack until the coupon strikes the opposite end of the pipe, after which the handwheel 64 is rotated backwardly a selected angle, which withdraws the coupon a selected distance. The handwheel is then locked by means 70 which comprises a spring driven pin which is adapted to lock into one of the holes 66 in the rim of the wheels 64. The holes 66 serve as indicia of the angle of rotation of the pinion shaft, and as a means of locking the pinion shaft against rotation. Thereafter, the coupon is left in position for a selected period of time and it is then removed.

In addition to the above described means of locating the coupon 46 with pipe 10 a stop (not shown) may be welded on rack 40 to limit the downward travel of the rack. A stop may also be welded to the upper end of the rack to make certain that it cannot go all the way past pinion 58.

In the process of removal of the coupon from the pipeline, the handwheel is unlocked, and rotated to withdraw the rack back into the cylinder 30. The valve 18 is then closed, sealing the pipeline pressure from the coupon holder 10. Since the interior space 31 of the coupon holder will be filled with pipeline fluid under pressure, the excess pressure is reduced by the pressure release means 38, after which the quick closure 36 is removed. The rack is further traversed outwardly of the chamber 30 until the end 47 of the rack reaches the pinion 48, after which the rack can be lifted out of the guide 42 and out of the chamber. The coupon can be inspected and/or changed as desired.

When the coupon is to be repositioned inside the pipeline, the rack is positioned between the guides 42 and 44 and moved longitudinally until the pinion is engaged, after which it is moved into the position shown in FIGS. 1 and 2, where the end closure can be attached so that the chamber 30 is sealed. The valve 18 is then opened and the handwheel 64 is rotated, rotating the pinion and driving the rack into the valve and the coupon into the pipeline.

In FIG. 3 is shown one embodiment of the means to support pinion shaft 56 in the flange 60, by means of an attached bushing 80 which has an internal diameter slightly larger than the external diameter of the shaft 56. Bearings can be installed in the bushing so if desired, as is well known in the art. A packing gland is provided with a seal ring 82 which can be compressed by means of a packing nut 84, as is well known in the art. Thus, by means of the special flange structure 60, the pinion shaft can be positioned in the cylinder 30 at the proper position and in operating relation with the rack 40.

Shown in FIG. 2 is a tapped boss 72 at the flange end of cylinder 30, which carries a pipe nipple and valve 74 carrying an outlet pipe 76. The purpose of the valve and pipe is to drain the interior space 31 of the cylinder, of the pipeline liquid which has previously filled the chamber 30. With the liquid drained, it is possible to examine the interior of the cylinder 30 prior to removal of re-entry of the rack 40. The use of elements 72, 74 and 76 is optional.

While the coupon holder has been illustrated in a vertical position, it can be mounted in a horizontal position as well as a vertical position. Of course, if it is in a horizontal position, there is no need of the draining feature comprising the valve 74 and the pipe 76. In that case, a plug would be put into the taped boss 72 and the operation would be as previously indicated.

FIG. 4 illustrated an alternate arrangement of the coupon holder which accomplishes the same results as the embodiment shown in FIGS. 1 through 3, but which may be more economically constructed. A tee 86 is positioned in pipeline 12. A short nipple 88 is used to connect valve 18A. Flange 32A which is welded to the lower end of cylinder 30A has a lower threaded end 32B which is threaded into the top of valve 18A. Rack guide 40A is supported within cylinder 30A by brackets 44A.

Side pipe 52A has an opening 52B therethrough which receives shaft 56A. A flange 54A is attached to the outer end of side pipe 52A. Indexing means 70A is attached to flange 54A.

The upper end of cylinder 30A is threaded and receives an internally threaded cap 90 which is removed when the coupon 46 is to be examined.

Side pipe 52A has a recess 92 in the inner end of diameter larger than the diameter of opening 52B. A collar 94 is coaxially attached to shaft 56A and rotates with the shaft in recess 92, the collar being of slightly smaller diameter than the internal diameter of recess 92. A gasket 96 is positioned between the collar 94 and the end wall of side pipe 52A, the gasket having an opening receiving shaft 56A. It can be seen that fluid pressure with cylinder 30A will force shaft 56A outwardly, urging increased contact pressure of collar 94 with gasket 96. In this way static thrust is vitalized to prevent leakage of fluid along shaft 56A.

Flange 54A has an enlarged internal diameter recess 98 surrounding opening 54B. Positioned in recess 98 is an O-ring gasket 100 which further assures leakproof support of shaft 56A.

The embodiment of FIG. 4 works the same way to achieve the same results as the arrangement of FIGS. 1 through 3, but uses inexpensive and more readily available components.

While the invention has been described with a certain degree of particularity, it is manifest that many changes may be made in the details of construction and the arrangement of components without departing from the spirit and scope of this disclosure. It is understood that the invention is not limited to the embodiments set forth herein for purposes of exemplification, but is to be limited only by the scope of the attached claim or claims, including the full range of equivalency to which each element thereof is entitled.

What is claimed:

1. A holder for inserting into and retrieving a corrosion coupon from a pipeline while under pressure comprising:
   (a) an upstanding elongated cylindrical chamber;
   (b) means at the lower end for sealing attachment of the chamber to a valve, which is itself attached as an upwardly extending side branch to a pipeline;
   (c) closure means at the upper end of said chamber for closing and sealing said chamber;
   (d) an elongated rack inside said chamber, and means to guide said rack for longitudinal motion;
   (e) insulating means at the lower end of said rack for support of a corrosion coupon;
   (f) a horizontal side pipe attached to said chamber;
   (g) a pinion shaft rotatably supported within said side pipe, the outer end extending sealably therefrom;
   (h) a pinion gear affixed to the inner end of said shaft within said chamber;
   (i) a handwheel affixed to said pinion shaft externally of said chamber, the handwheel having equally spaced detent holes on the peripheral suface thereof; and
   (j) a spring driven pin slidably supported to said side pipe, the pin engaging detent holes in said handwheel to lock said handwheel in selectable positions, said rack means and insulation means being contained fully within said chamber when said rack means is fully upwardly withdrawn.

2. The coupon holder as in claim 1 including valve means to bleed the fluid pressure inside said chamber to atmospheric pressure.

3. The coupon holder as in claim 1 including valve means to drain liquid from said chamber.

* * * * *